United States Patent [19]

Junker-Buchheit et al.

[11] Patent Number: 5,773,576
[45] Date of Patent: Jun. 30, 1998

[54] CODED THIN LAYER CHROMATOGRAPHY SUPPORT

[75] Inventors: Andrea Junker-Buchheit, Bad König; Heinz-Emil Hauck, Gross Umstadt; Willi Jost, Langen, all of Germany

[73] Assignee: Merck Patent Gesellschaft mit Beschrankter Haftung, Germany

[21] Appl. No.: 612,882

[22] PCT Filed: Aug. 30, 1994

[86] PCT No.: PCT/EP94/02871

§ 371 Date: May 15, 1996

§ 102(e) Date: May 15, 1996

[87] PCT Pub. No.: WO95/07459

PCT Pub. Date: Mar. 16, 1995

[30] Foreign Application Priority Data

Sep. 9, 1993 [DE] Germany .......................... 43 30 564.4

[51] Int. Cl.⁶ .................................................. G01N 30/90

[52] U.S. Cl. .................. 422/70; 73/61.54; 210/198.3; 210/658; 422/56; 422/57; 436/162; 347/225

[58] Field of Search ........................... 436/162; 73/61.54; 210/658, 198.3; 422/70, 56, 57; 347/225

[56] References Cited

U.S. PATENT DOCUMENTS 4,126,554  11/1978  Rainin ................................... 210/198.3
4,960,691  10/1990  Gordon et al. .......................... 436/162

OTHER PUBLICATIONS

Pfeufer et al., Kunstoffe vol. 79 No. 6 issued Jun. 1989 pp. L43–L46.

*Primary Examiner*—Jan Ludlow
*Attorney, Agent, or Firm*—Millen, White, Zelano & Branigan, P.C.

[57]  ABSTRACT

Support materials for thin-layer chromatography characterized by a marker code applied using laser light.

9 Claims, No Drawings

CODED THIN LAYER CHROMATOGRAPHY SUPPORT

The invention relates to a coded support for thin layer chromatography ("TLC") and to a process for its production.

The developments on modern analysis methods are ever increasing, for example with regard to accuracy, reproducibility, unambiguous assignment and documentation of analysis results. Thus, the increasing demands for documentation have been met, for example, in guidelines such as DIN-ISO 9000, Good Manufacturing Practice (GMP) or Good Laboratory Practice (GLP).

It is correspondingly necessary to individually mark or code even ready-prepared layers in TLC during and after their chromatographic use, and therefore make them impossible to mistake for each other.

Such a marking should have the highest possible information density and be capable of being applied quickly onto or into the respective layer. Above all, however, it should be resistant to all organic and inorganic solvents, bases and acids (not only in liquid form, but also in the case of gas-phase action as a result of vaporization) which are conventionally used in TLC so that neither the chromatographic development nor the result of the separation is disrupted or affected. In addition, the marking should be readable not only in daylight but also under UV illumination (for example 254 and 366 nm).

The markings conventionally used to date, for example by sticking on labels or inscriptions in the carrier layer, satisfy these requirements only partially or not at all, and are also laborious. As a result of manual data transfer, transfer errors can make the entries unusable. Labels can become detached and be lost.

The object of the invention was to provide marked (coded) TLC supports which present the specified disadvantages not at all or only to a lesser extent.

It was surprisingly found that the intended result can be achieved by exposing the support to laser light, a corresponding template being used (for example numbers and/or letters or else lines for bar coding) or the laser being controlled by means of a computer. This produces a permanent mark which is easy to read in daylight and under UV light. When the laser is controlled by means of a computer, no templates are required.

The subject of the invention is correspondingly a TLC support characterized by a coding applied by means of laser light, and a process for its production, characterized in that a conventional TLC support is exposed to laser light.

Supports are primarily glass plates and foils (for example aluminum foils or plastic films, for example those made of polyterephthalate), which are coated with sorbent and contain a binder as well as, optionally, a fluorescent indicator and/or further additives.

All stationary phases conventionally used in TLC are suitable as sorbents, preferably modified or unmodified silica gels, as well as, for example, celluloses, polyamides, diatomaceous earth, aluminum oxides.

Polymeric organic substances are preferably used as binders, for example polyacrylic acid or polymethacrylic acid, and amides thereof.

A pulsed or continuous $CO_2$ laser (wavelength 1.06 $\mu$m) or a Yag laser (solid-state laser, wavelength 10.6 $\mu$m) is preferably used as the laser source. The exposure time is typically equal to 5–50 nanoseconds per symbol.

The coding obtained may contain any data, for example logo of the producer company, item number, batch number, date of production, unique individual numbering (serial numbering).

Coding is preferably carried out by exposing the sorbent layer, which contains a binder. It is, however, also possible to make a laser inscription on the uncoated back of a support glass plate or a coated plastic film. In the case of a glass plate, the exposure produces fine thermal stress cracks which causes opaqueness of the glass surface that can be discerned in the visible light wavelength range.

Even without further comments, it will be assumed that a person skilled in the art can use the above description in the widest scope. The preferred exemplary embodiments should therefore be taken merely by way of description, without any limitation being implied.

The full disclosure of all applications, patents and publications referred to above and below, and of the corresponding application DE 43 30 564, filed on 09 Sep. 1993, are included in this application by reference.

EXAMPLES

Example 1

A ready-prepared HPTLC plate (E. Merck silica gel 60 $F_{254}$, item No. 5642, 100×200 mm) is exposed to a pulsed $CO_2$ laser, wavelength 10.6 $\mu$m, exposure time respectively 50 nanoseconds for each individual symbol. In this case a mask is used, which covers most of the plate, except for the openings for the desired symbols; the plate being moved in such a way that each individual exposure is incident at the point for the respectively desired symbol.

Example 2

A ready-prepared HPTLC plate (E. Merck silica gel 60, item No. 5641, 100×200 mm) is inscribed on using a continuous $CO_2$ laser (wavelength 10.6 $\mu$m, power consumption 10 watts, speed of advance 100 mm/sec). In this case the laser is controlled using a computer.

We claim:

1. A coded thin layer chromatography material which comprises a support coated with a sorbent layer consisting essentially of sorbent particles and a binder wherein the sorbent layer has an alphanumeric identifier or a bar coding thereon formed by a process consisting essentially of exposing the sorbent layer to laser light in an alphanumeric or bar coding pattern such that the coding is readable in either visible or ultraviolet light.

2. The thin layer chromatography support of claim 1, wherein the support comprises a glass plate, foil or plastic film.

3. The thin layer chromatography support claim 1, wherein the sorbent particles are of modified or unmodified silica gel, cellulose, polyamide, diatomaceous earth or aluminum oxide material.

4. The thin layer chromatography support of claim 1, wherein the sorbent particles are of modified or unmodified silica gel material.

5. The thin layer chromatography support of claim 1, wherein the binder is a polyacrylic acid, polymethacrylic acid or an amide thereof.

6. A process for coding a thin layer chromatography material comprising a support having a sorbent layer thereon consistng essentially of sorbent particles and a binder, which process consists essentially of exposing the sorbent layer to laser light in an alphanumeric or bar coding pattern to produce an alphanumeric or bar coding thereon which is readable in either visible or ultraviolet light.

7. The process of claim 6, wherein the laser light is from a pulsed or continuous $CO_2$ laser or Yag laser.

8. The process of claim 6, wherein the exposure time of the laser light is 5 to 50 nanoseconds per coding symbol.

9. The process of claim 6, wherein the laser light is directed by computer to apply the coding.

* * * * *